(12) United States Patent
Dales et al.

(10) Patent No.: US 9,360,407 B2
(45) Date of Patent: Jun. 7, 2016

(54) RADIATION DETECTOR FOR DENSITY OR LEVEL MEASUREMENTS

(71) Applicant: JOHNSON MATTHEY PUBLIC LIMITED COMPANY, London (GB)

(72) Inventors: Kevan Bradley Dales, Cleveland (GB); Timothy Hough, Durham (GB); Geoffrey Stuart Howe, Durham (GB)

(73) Assignee: JOHNSON MATTHEY PUBLIC LIMITED COMPANY, London (GB)

( * ) Notice: Subject to any disclaimer, the term of this patent is extended or adjusted under 35 U.S.C. 154(b) by 0 days.

(21) Appl. No.: 14/423,908

(22) PCT Filed: Sep. 5, 2013

(86) PCT No.: PCT/GB2013/052332
§ 371 (c)(1),
(2) Date: Feb. 25, 2015

(87) PCT Pub. No.: WO2014/037731
PCT Pub. Date: Mar. 13, 2014

(65) Prior Publication Data
US 2015/0241327 A1 Aug. 27, 2015

(30) Foreign Application Priority Data
Sep. 6, 2012 (GB) .................... 1215920.8

(51) Int. Cl.
*G01N 9/24* (2006.01)
*G01F 23/288* (2006.01)
*G01T 1/18* (2006.01)

(52) U.S. Cl.
CPC ............... *G01N 9/24* (2013.01); *G01F 23/288* (2013.01); *G01F 23/2885* (2013.01); *G01T 1/18* (2013.01)

(58) Field of Classification Search
CPC ............... G01F 23/288; G01F 23/2885
USPC ........................................... 250/336.1
See application file for complete search history.

(56) References Cited

U.S. PATENT DOCUMENTS

| 4,245,479 | A | * | 1/1981 | Richter et al. ............ 62/119 |
| 5,025,160 | A | * | 6/1991 | Watt ..................... 250/356.1 |
| 6,633,625 | B2 | * | 10/2003 | Jackson et al. ............ 378/54 |
| 7,128,812 | B1 |  | 10/2006 | Cupit |
| 2004/0025569 | A1 |  | 2/2004 | Damm et al. |
| 2011/0044427 | A1 | * | 2/2011 | Featonby et al. .......... 378/52 |

(Continued)

FOREIGN PATENT DOCUMENTS

| DE | 19922381 A1 | 11/2000 |
| DE | 19926388 A1 | 12/2000 |

(Continued)

OTHER PUBLICATIONS

International Search Report, dated Dec. 5, 2013, from corresponding PCT application.
GB Search Report, dated Dec. 21, 2012, from corresponding GB application.
GB Search Report, dated Jan. 30, 2014, from corresponding GB application.

*Primary Examiner* — Marcus Taningco
(74) *Attorney, Agent, or Firm* — Young & Thompson

(57) ABSTRACT

A nucleonic density profiler includes a detector probe, for detecting ionizing radiation, includes an array of sources of ionizing radiation, an array of radiation detectors and a circuit board including at least two circuit board portions. A power source and electronic apparatus includes a control unit and a signal and data processor for calculating a density profile of the material phases using signals generated by the detectors in response to radiation received from the radiation sources.

14 Claims, 2 Drawing Sheets

(56) References Cited

U.S. PATENT DOCUMENTS

Figure 1:
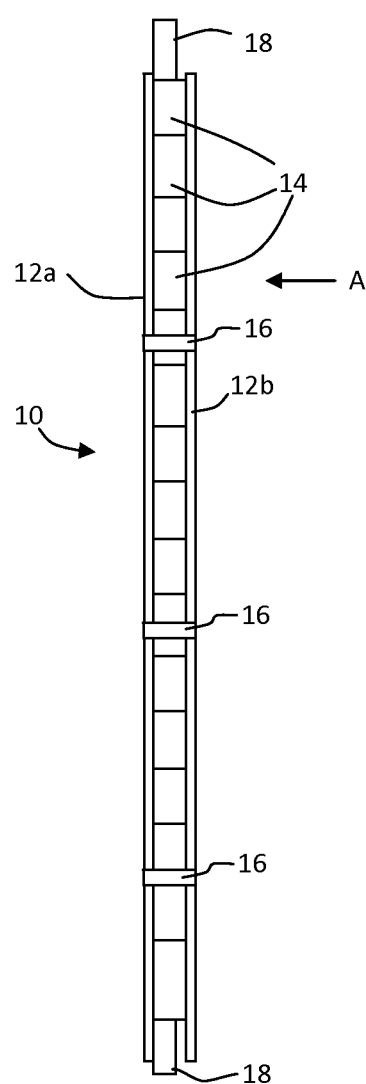

2011/0048125 A1* 3/2011 Jackson et al. ............. 73/290 R
2011/0192983 A1   8/2011 Yu et al.
2011/0220800 A1* 9/2011 Featonby et al. .......... 250/357.1
2012/0256086 A1* 10/2012 Husebo et al. ............. 250/307
2014/0175290 A1* 6/2014 Field et al. ................ 250/361 R

FOREIGN PATENT DOCUMENTS

| GB | 2349504 A | 11/2000 |
| JP | 2003084068 A1 | 3/2003 |
| WO | 00/22387 A1 | 4/2000 |
| WO | 03/046610 A1 | 6/2003 |
| WO | 2010/032064 A1 | 3/2010 |

* cited by examiner

RADIATION DETECTOR FOR DENSITY OR LEVEL MEASUREMENTS

BACKGROUND OF THE INVENTION

1. Field of the Invention

The present invention relates to an apparatus for measuring levels of materials, especially of fluids, and optionally for calculating a density profile of a mixed fluid system.

2. Description of the Related Art

A density profiler has been described in WO2000/022387. The device comprises a linear array of sources of ionising radiation which emit radiation towards detectors disposed in one or more linear arrays. When the source array and detector array(s) are positioned so that they traverse the interfaces between two or more fluids in a container, the interfaces of the fluids may be identified from the differences in radiation received by each detector in the array. The device has been successfully deployed for use in storage tanks and oil separators. A desirable feature of the profiler device is its compact diameter which enables it to be fitted into a vessel through a standard access port. In some circumstances it is desirable to reduce the cross-section of the profiler device even more in order to access installations in which the size of the port or the space around the port makes installation particularly difficult. Also the reduction in size of the detector arrays can allow thicker dip pipes or additional thicknesses of insulating materials to be used. It is therefore an object of the invention to provide a density profiler in which the detector array(s) are relatively small compared with known devices.

SUMMARY OF THE INVENTION

According to the invention, we provide a detector probe for use in a nucleonic instrument, comprising an array of radiation detectors mounted on a circuit board characterised in that said circuit board comprises at least two portions, each portion being aligned substantially parallel to the longitudinal axis of said array and each of said portions being in a different plane from each other portion.

According to the invention, we provide a nucleonic instrument for measuring a density or level of one or more material phases within a container, comprising:
 (a) an array of sources of ionising radiation,
 (b) at least one detector probe for detecting ionising radiation comprising an array of radiation detectors mounted on a circuit board,
 (c) a power source, and electronic apparatus comprising a control unit and a signal and data processing means for calculating a density profile of the material phases using signals generated by the detectors in response to radiation received from the radiation sources; the power source and electronic apparatus being housed within an enclosure supported mounted adjacent to the detector probe,
characterised in that said circuit board comprises at least two portions each portion being aligned substantially parallel to the longitudinal axis of said array and each of said portions being in a different plane from each other portion.

At least two powered circuits are present in the detector probe to deliver power to the detector(s), to enable control signals to pass to the detector from a control unit and to carry data signals from the detector to a signal processor and data processor. The powered circuits are carried on a circuit board, preferably a printed circuit board. The circuit board comprises at least two portions which may be separate or joined together along at least a portion of their length. When the circuit boards are joined they may form an angle, for example between about 30 and about 150 degrees. In a preferred form, the portions of the circuit board are not joined along their entire length. Preferably the circuit boards are not joined together along any part of their length. More preferably, they are spaced apart from each other, optionally separated by one or more radiation detectors. Preferably one or more radiation detectors are mounted between two or more circuit board portions Preferably the detector probe is intrinsically safe. "Intrinsically safe" is a standard term of the art of electrical devices. Intrinsically safe apparatus is intended for use in an explosive or potentially explosive atmosphere. In intrinsically safe electrical equipment, the electrical circuits themselves are incapable of causing an explosion in the surrounding explosive atmospheres. Intrinsically safe apparatus refers to electrical equipment in which all the circuits are intrinsically safe circuits. An intrinsically safe circuit is a circuit in which any spark or any thermal effect produced in conditions which include normal operation and specified fault conditions is not capable of causing ignition of a given explosive atmosphere. The design and selection of components and the test criteria applied to such equipment is governed by national and international standards such as BS EN 60079-11:2012 and its related parts, including part 0 concerning general requirements for electrical equipment intended for use in explosive atmospheres.

Preferably the detector probe conforms at least to Level of Protection ib of the standard, i.e. it is designed to be safe in use in explosive atmospheres in normal operation and with the application of those non-countable faults which give the most onerous condition; and in normal operation and with the application of one countable fault plus the application of those non-countable faults which give the most onerous condition as defined in section 5.3 of BS EN 60079-11:2012. Countable faults and non-countable faults are defined in BS EN 60079-11:2012 at paragraph 3.7. Most preferably, the detector probe conforms to Level of Protection is of the standard, i.e. it is designed to be safe in use in explosive atmospheres when the circuit contains two countable faults as defined in section 5.2 of BS EN 60079-11:2012. Such protection is achieved by the use of various components and construction methods which include, for example, the separation of parts of the circuits by minimum separation distances as set out in section 6.3 "Separation Distances" of BS EN 60079-11:2012. The minimum separation distances required to achieve intrinsic safety affect the size, especially the minimum width of the portions of the circuit board. In general it is preferred that the circuit boards are as narrow as possible, given the constraints of the design of the circuits, in order that the detector probe may have as small a cross-section as possible. In general, however, the radiation detectors themselves have a particular diameter and there is little advantage to be gained in providing a portion of the circuit board which is narrower than the diameter of the radiation detector. In a preferred embodiment the radiation detector has a diameter of 15-20 mm. Preferably each circuit board has a maximum width of not greater than 40 mm, especially not greater than 30 mm. Each circuit board preferably has a thickness of from mm-3 mm.

Each portion of the circuit board may have mounted thereon different electrical components and connections. Different types of components may be grouped so that each portion of the circuit board carries a different set of components from each other portion of the circuit board. One such portion may be configured to handle control and measurement signals to and from the detector, whilst the other is configured to provide electrical power to the detector. For example, one portion of the circuit board may carry one or more high voltage cables for supplying power to the radiation detectors. Another portion of the circuit board may carry low voltage control and/or data signals between the detectors and a control unit and/or signal processing unit. Provision of the high voltage (>50V) circuit on a different portion of the circuit board from the portion carrying the low voltage (<50V) circuits may facilitate the design of the probe to meet the required standard for intrinsic safety because the minimum separation of the circuits specified by the standard for achieving intrinsic safety may be achieved.

The circuit board portions may be electrically insulated from each other, from the radiation detector(s) and/or other components of the detector probe by the use of electrically insulating material. The detector probe may also include thermal insulation. When a heat pipe, heater or other thermal equipment is provided to adjust the temperature of the detector probe, then thermally conductive material may be provided between such equipment and the parts of the detector probe which are intended to be heated or cooled by such equipment. For example, when the detector probe is liable to be subjected to temperatures that are below the optimum operating range of the electronics and/or the detectors, a source of heat such as electrical trace heating may be provided in the detector probe. Materials such as the Sil-Pad™ range of materials supplied by the Bergquist company are thermally conductive and electrically insulating and may be used in the detector probe.

In a preferred embodiment of the invention, the detector probe additionally includes an elongate support structure extending along at least part of the length of the detector array to provide additional strength and stiffness to the detector array. In one form of the invention, the elongate support structure comprises a rod or plate to function as a support, preferably formed from a stiff material such as metal or reinforced resin. The elongate support preferably extends along the greater part of the length of at least one of the circuit board portions. More preferably, the elongate support extends along substantially the entire of the length of at least one of the circuit board portions, so that the circuit board portion(s) are supported along substantially the entire of their length. The detectors and circuit board are preferably mounted on the support. When the detector probe is for use in a density profiler instrument, or another such instrument in which the correct alignment of an array of radiation sources and the detector probe affects the accuracy of the instrument, the support is preferably formed from a material which has a similar coefficient of expansion as the material supporting the radiation sources of the source array. In this form, the expansion and contraction of the detector array as a response to a change in its temperature matches the expansion or contraction of the source array so the sources and detectors remain aligned even if subjected to a change in temperature. In an alternative form of this embodiment, the elongate structure comprises a functional device such as a conduit or a heat pipe. If a conduit is provided for carrying cables then it may be used to form a support structure for the detector array.

A heat pipe is useful for maintaining the temperature of the detector probe within a desired range. This is desirable in environments where the detector probe is to be used in conditions where the ambient temperature may exceed the recommended operating temperature of the radiation detectors or their associated electronic apparatus. The provision of a heat pipe enables heat to be transferred from a relatively hot part of the detector array to a cooler location. The heat pipe may operate to remove heat from the space surrounding the detectors. In one embodiment of the invention, the detectors are mounted in thermal contact with a heat pipe. In this embodiment, the detectors may be physically supported on the heat pipe, for example using means such as adhesive, a strap, clip, cable-tie or other connector. When the detectors are directly mounted in thermal contact with a heat pipe, heat can be removed from the detectors efficiently. In this embodiment, the detectors are preferably electrically isolated from the heat pipe by means of a material which is both thermally conductive and electrically insulating. Such materials include grease, mica and composite materials such as the Sil-Pad™ range of materials. Separate portions of circuit board may be mounted radially externally of the detectors and support. In this way the circuit board components may be arranged so that they are physically separated by the support, the insulation and the detectors to the maximum extent.

The detector probe comprises at least one detector for detecting ionising radiation emitted by a radiation source. The type of detector used may be selected by the person skilled in nucleonic instrument engineering, having regard to the properties of the radiation to be detected, the conditions in which the detector is to be used and the characteristics of radiation which are to be measured. Typically the detectors used are gaseous ionisation detectors, such as Geiger Müller tubes, or scintillation devices including scintillation crystals and organic scintillators. Geiger Müller tubes are preferred detectors for the detector probe of the present invention because of their robustness and wide range of operating temperature. The detector probe may include one detector or more than one detectors, depending on the intended use of the detector probe. When the detector probe is for use in a level gauge or density profiler, it typically has at least 4, preferably at least 10 detectors. Density profilers for use in large vessels may require detector probes including at least 20 detectors, more preferably at least 40 detectors, for example about 100 detectors, spaced apart and preferably arranged as a linear array of detectors. The size of the detectors affects the precision of level detection when the probe is used in a level gauge or density profiler. Therefore the size of detector(s), and their spacing, if more than one detector is used, is selected according to the demands of the use for which the detector probe is designed. When the detector probe is used to find a level (including in a density profile) with high precision then small detectors set in close proximity to each other are preferred. Suitable small Geiger Müller tubes have a diameter of from 10 mm to 25 mm, more preferably <20 mm. The detectors may have a length of from about 25 mm to >200 mm. Precision of a level gauge or density profiler can be increased by including overlapping detectors, which may be present in separate detector probes.

The detector probe comprising the detectors, circuit boards and optional support, is preferably surrounded by a protective layer, such as a plastic tube. The detector probe comprising the detectors, circuit boards and optional support, all optionally surrounded by a protective layer, is preferably housed within a protective housing, preferably formed from a tough and rigid material. The housing is made from a material which is sufficiently transparent to the radiation to be detected by the detectors for the detector probe to perform its function. A suitable material for the housing is titanium which can be formed to be sufficiently strong at a thickness which remains substantially transparent to gamma radiation. In use the detector probe may be placed within a dip tube or dip pipe. The detector probe may further comprise a thermally insulating material arranged between the detectors and the electronic components of the probe and an external housing of the detector probe in order to help maintain the temperature of the detectors within a desired range of temperatures. Normally the insulation is provided in as thin a layer as possible, in order to reduce the dimensions of the probe. For this reason, insulating materials having a very low thermal conductivity are preferred. A preferred form of detector probe, suitable for use in a density profiler, comprises two portions of an electrical circuit board, a plurality of radiation detectors and an elongate support, all enclosed within a rigid housing, and thermal insulation between the inner wall of the housing and the detectors.

The skilled person will appreciate that the selection of a suitable thermal insulating material is dependent upon the characteristics required. In one embodiment, we have found that a suitable thermal insulator has a thermal conductivity ($\kappa$)<0.05 W/m/K, and especially <0.005 W/m/K. The insulation may or may not include evacuated compartments. We have, however, found that the materials used to form such panels may not be capable of maintaining a vacuum at high temperatures. The insulation may include metallised portions.

The electronic apparatus associated with a nucleonic instrument according to the invention, comprising the control system, signal and data processing device, power source and optionally equipment such as data loggers and transmitting equipment, is normally housed within an enclosure in order to protect it from the environment. The enclosure is designed to withstand the conditions in which the instrument may be deployed, including those of super-ambient temperature and pressure. The temperature of the electronic apparatus within the enclosure is desirably maintained within a temperature range in which it can operate according to its designed function. Preferably the electronic apparatus is maintained at a temperature less than 120° C., more preferably less than 100° C. A temperature sensor may be provided to monitor the temperature at one or more locations within the enclosure. The enclosure may be supported mounted adjacent to the detector probe and source array or may alternatively be mounted in a position which is spaced apart from the detector probe and source array. In the latter case, communication means, which may be wireless or wired, are provided to carry electrical signals between the detector probe and the electronic apparatus. The detector probe tends to conduct heat to or away from any associated electrical control system or data processing apparatus. When the detector probe is subjected to very high temperatures a corresponding increase in the temperature of associated apparatus may be reduced by means of thermal insulation placed between the detector probe and the associated apparatus. The enclosure may contain insulation material in order to thermally insulate the electronic apparatus from heat conducted by the detector probe and/or the source array, and/or to insulate the electronic apparatus from hot or cold external temperatures. In a preferred embodiment, the instrument comprises thermal insulation between the detector probe on the one hand and the power source and electronic apparatus on the other hand. In this way the electronic control, signal/data processing components and power source may be protected from high temperatures which might adversely affect their operation.

The nucleonic instrument of the invention comprises a source of ionising radiation and a detector probe as hereinbefore described, said source and detector probe being arranged so that ionising radiation from the source passes along a straight line through a portion of the container to the detector probe. The source is mounted within a radiation shielding material which includes collimation means for producing a collimated beam of radiation which is directed towards the detectors. The source and/or detector probe may be mounted outside or inside a vessel containing the material to be measured. When the source is mounted outside the vessel and the radiation is to traverse at least one vessel wall, the source must be selected to produce radiation of sufficient energy to penetrate the walls of the vessel. The source should also be selected to be of sufficient activity to produce sufficient counts in the detector(s) in order that a reproducible signal may be generated by the detectors which is proportional to the radiation detected within about a second so that level measurement may be carried out reasonably quickly.

When the nucleonic instrument is a level gauge, intended for detecting the location of a level of material within a vessel, one or more than one sources may be used. Normally the number of sources used is not more than 10 and is preferably from 1-4. Each source may emit a beam of radiation towards more than one detector, generally from 4-10 detectors. From 2→100 detectors may be used, depending on the size/detection area of each detector and the resolution required of the apparatus.

When the nucleonic instrument is a density profiler, for measuring a level of two or more material phases within a container, the source of radiation comprises a linear array of sources of radiation. At least one detector probe according to the invention is provided for detecting ionising radiation. The provision of more than one detector probe is particularly advantageous when the nucleonic instrument is a density profiler. A signal and data processing means is provided for calculating a density profile of the material phases using signals generated by the detectors in response to radiation received from the sources. The source array and detector probe(s) are arranged so that ionising radiation from each source passes along a straight line through a portion of the container to a detector carried on the detector probe. The sources are collimated to provide at least one beam of radiation, each beam being directed to one detector located on a detector probe. The relative attenuation of the beams of radiation detected by different detectors, which are located at different positions in the material phases, may be used to calculate a density profile of the material phases.

The source array includes a plurality of radiation sources, which are preferably sources of gamma radiation. The energy of the source radiation is typically not more than about 1400 keV and is desirably lower than this. Preferably the energy of the source radiation is not less than about 30 keV. The source can be a radioactive isotope as described above in connection with the level gauge. When the instrument is intended to be fitted into a vessel such as an oil separator through a standard port, the beam length is preferably less than 50 cm, more preferably less than 30 cm and for this use a less energetic source is thus desirable and energies of less than 500 keV, particularly less than 300 keV and optimally less than 100 keV, are desirable in this invention. Suitable low-energy sources include in particular $^{241}$Am which is a 60 keV gamma source. For higher energy sources such as $^{137}$Cs, a greater path length is optimal, typically between 20 cm and 40 cm, e.g. about 30 cm. Other radioisotope sources can be used if desired. The use of low-energy sources makes equipment handling and source shielding safer and/or easier. The source radiation could be X-rays but preferably comprises or consists of alpha particles, beta particles, gamma radiation and/or neutrons, more preferably gamma radiation.

The source shielding and collimation means is shaped so that the emission of radiation is confined, so far as possible, to a beam of suitable width directed through the fluid medium towards one or more detectors. Normally this is achieved by providing a channel or aperture through the shielding material surrounding the source such that emission of radiation from the source is substantially confined to emission of a beam of radiation through the channel. It is often desirable to collimate the source radiation into more than one beam, e.g. by providing more than one channel in the shielding material, so that radiation from a single source may be directed at more than one detector. In this case, the detectors may be in different positions within or outside the vessel and they may form part of the same linear array or they may be located in different detector probes.

BRIEF DESCRIPTION OF THE DRAWING FIGURES

Figure 1A:
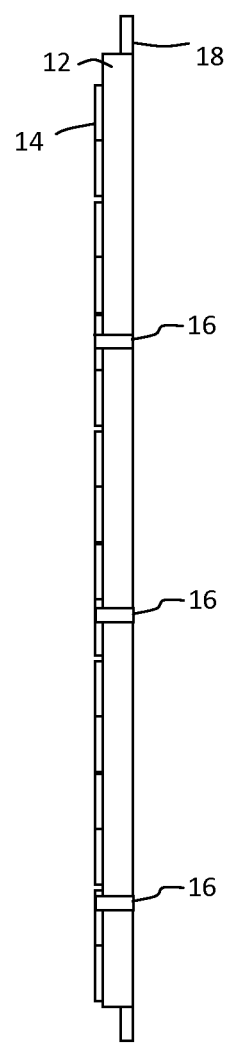
Figure 2:
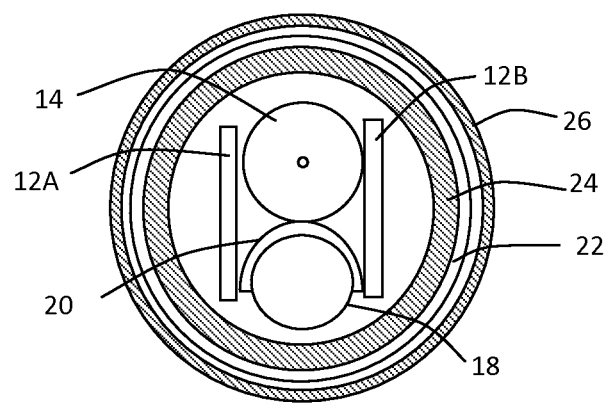
Figure 3:
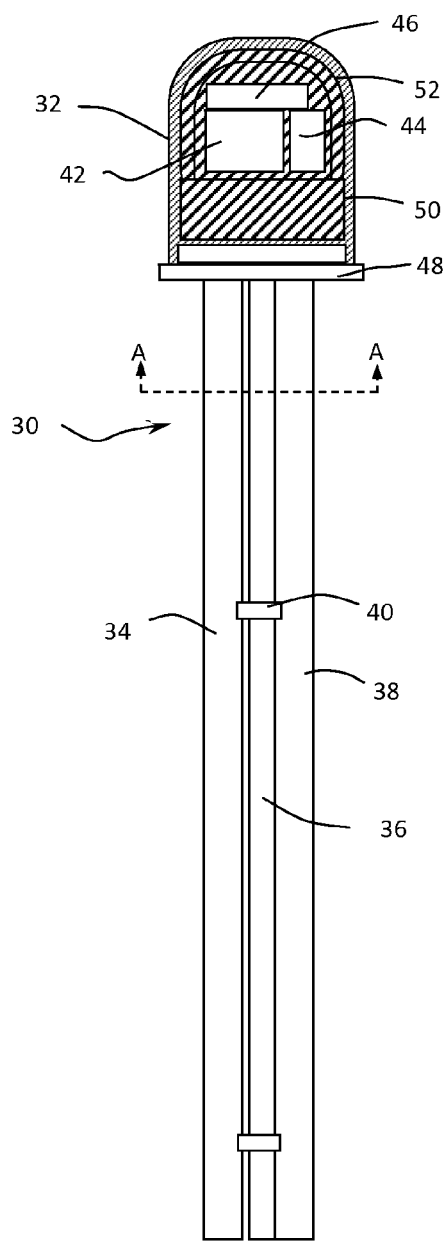
Figure 4:
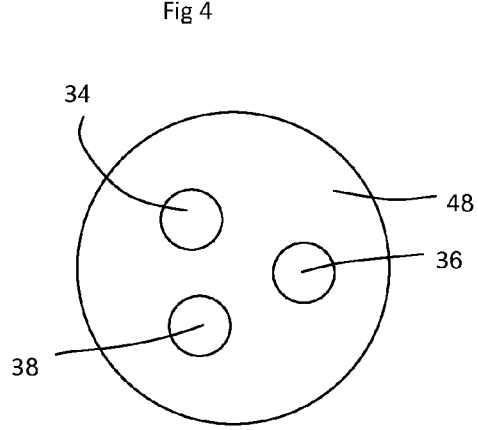

The invention is further described, by way of example only, with reference to the accompanying drawings, which are:

FIG. 1: A schematic diagram of a detector probe used in the instrument according to the invention;

FIG. 1A: A schematic diagram of a side view, from direction A, of the detector probe in FIG. 1;

FIG. 2: A schematic diagram of transverse section through a detector probe according to the invention;

FIG. 3: a schematic sectional view through a nucleonic instrument according to the invention; and FIG. 4: a section through line A-A of FIG. 3.

DETAILED DESCRIPTION OF THE INVENTION

FIGS. 1 & 1A show a detector probe 10, comprising two printed circuit boards 12a and 12b. A plurality of detectors 14 are mounted on the circuit boards in a linear arrangement. A steel rod 18 provides stiffness to the probe assembly. Straps 16 hold the assembled components together securely. A section through the detector probe, housed within a dip tube, is shown in FIG. 2. The detector probe is installed within a protective plastic tubular enclosure 22 which is housed within a cylindrical dip pipe 26. Thermal insulation 24 is provided inside the tube 22.

FIG. 3 shows an elevation of a density profiler instrument 30 according to a preferred embodiment of the invention. The instrument comprises a steel housing, shown in section, comprising a flanged support structure 48 and a domed cover 32. The housing contains at least a high voltage generator 42, data loggers, counters, signal processing means and data processors 44, means for supplying power to the voltage generator 46 and electrical equipment and means for transmitting information between the data processors and an external location. A layer of insulation 50 is packed between the electrical equipment contained in the housing and the support bracket 48 to which the dip tubes 34, 36 and 38 are mounted. Further insulation 52 is provided around the inside walls of the housing. A source array is housed in tube 34 and two detector probes are housed in tubes 36 and 38. The tubes are braced together for stability by braces 40. The domed cover 32 in which the electronic and power equipment are housed is located directly above the tubes 34, 36 and 38, supported on a flange 48. Electrical connections, including power and data cables pass between the components in the housing and detector probes housed in tubes 36 and 38 through a conduit in flange 48. FIG. 4 shows a transverse section through the instrument along lines A-A and shows the configuration of the tubes 34, 36, 38 relative to each other and the housing support flange 48.

The invention claimed is:

1. A nucleonic instrument for measuring a density or level of one or more material phases within a container, comprising:
    (a) an array of sources of ionising radiation,
    (b) at least one detector probe for detecting ionising radiation comprising an array of radiation detectors mounted on a circuit board,
    (c) a power source, and electronic apparatus comprising a control unit and a signal and a data processor adapted for calculating a density profile of the material phases using signals generated by the detectors in response to radiation received from the radiation sources; the power source and electronic apparatus being housed within an enclosure supported mounted adjacent to the detector probe,
wherein said circuit board comprises at least two circuit board portions spaced apart from each other, one or more radiation detectors being mounted between said portions, one said circuit board portion carrying a high voltage circuit, another of said circuit board portions carrying a low voltage circuit and does not carry a high voltage circuit, and each portion being aligned substantially parallel to the longitudinal axis of said array and each of said portions being in a different plane from each other portion.

2. The nucleonic instrument according to claim 1, wherein said one or more detectors comprise Geiger Müller tubes.

3. The nucleonic instrument according to claim 1, comprising at least four detectors.

4. The nucleonic instrument according to claim 1 which is intrinsically safe, as defined by BS EN 60079-11:2012.

5. The nucleonic instrument according to claim 1, wherein said detector probe further comprises an elongate support.

6. The nucleonic instrument according to claim 1, wherein said detector probe further comprises a heat pipe.

7. The nucleonic instrument according to claim 1, comprising more than one detector probe.

8. The nucleonic instrument according to claim 1, wherein said one or more detectors have a diameter of 15-20 mm.

9. The nucleonic instrument according to claim 1, wherein each said circuit board portion has a thickness of 1-3 mm.

10. The nucleonic instrument according to claim 1, wherein the high voltage is greater than 50V.

11. The nucleonic instrument according to claim 1, wherein the low voltage is less than 50V.

12. The nucleonic instrument according to claim 1, wherein a rod is between the at least two circuit board portions.

13. The nucleonic instrument according to claim 1, wherein the detector probe is installed within a protective plastic tubular enclosure which is housed within a cylindrical dip pipe.

14. The nucleonic instrument according to claim 1, wherein thermal insulation is provided within the tubular enclosure.

* * * * *